United States Patent [19]

Strolle

[11] 4,334,075

[45] Jun. 8, 1982

[54] OXAZOLINE DIESTERS

[75] Inventor: Clifford H. Strolle, Springfield, Pa.

[73] Assignee: E. I. Du Pont de Nemours and Company, Wilmington, Del.

[21] Appl. No.: 189,060

[22] Filed: Sep. 22, 1980

[51] Int. Cl.³ ............................................ C07D 263/14
[52] U.S. Cl. ..................................... 548/239; 526/260
[58] Field of Search .......................................... 548/239

[56] References Cited

U.S. PATENT DOCUMENTS

| | | | |
|---|---|---|---|
| 2,559,440 | 7/1951 | Jordan et al. | 260/404.5 |
| 3,248,397 | 4/1966 | Purcell | 260/307 |
| 3,488,307 | 1/1970 | Walus et al. | 548/239 |
| 3,652,513 | 3/1972 | Gagliardi | 548/239 |
| 3,678,065 | 7/1972 | Frump | 260/307 |
| 3,962,270 | 6/1976 | Arlt | 260/307 |

FOREIGN PATENT DOCUMENTS

| | | | |
|---|---|---|---|
| 2076431 | 10/1971 | France | 548/239 |
| 2079970 | 11/1971 | France | 548/239 |

Primary Examiner—Anton H. Sutto

[57] ABSTRACT

An oxazoline diester capable of rapid air-drying is formed by esterifying the reaction product of a carboxylic acid having non-terminal, alpha, beta unsaturation and tris(hydroxymethyl) aminoethane with a second carboxylic acid. The oxazoline diester can be used as a reactive diluent in an air-drying coating composition or can be homo- or co-polymerized with other ethylenically-unsaturated monomers to form a useful resin for other coating systems.

9 Claims, No Drawings

OXAZOLINE DIESTERS

BACKGROUND OF THE INVENTION

1. Field of the Invention

This invention relates to oxazoline diesters, particularly to those in which the oxazoline ring is formed from tris(hydroxymethyl) aminomethane and a non-terminally unsaturated acid such as crotonic acid and in which the diester portion is derived from drying-oil fatty acids.

2. Description of the Prior Art

Oxazolines of the general formula

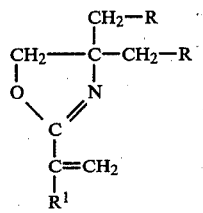

are well known for use as drying oils either in monomeric form or in polymeric form, after homopolymerization or co-polymerization with dissimilar ethylenic monomers. In the above formula, R is the carboxylate-ion portion of a carboxylic acid and $R^1$ is hydrogen, alkyl, or alkenyl. Such oxazolines and polymeric drying oils based thereon are shown, for instance, in U.S. Pat. No. 3,248,397 to Purcell.

The older methods of producing the monomeric oxazolines involved reacting an aminohydroxy compound and a carboxylic acid, and then condensing this reaction product with an aldehyde. This last step of condensing with an aldehyde was performed to yield the vinyl group in the position alpha to the ring.

Another method of producing the monomeric oxazolines with an alpha vinyl group is shown in U.S. Pat. No. 3,678,065 issued July 18, 1972 to Frump. This method involves reacting tris(hydroxymethyl) aminomethane, for example, with acrylic or methacrylic acid, yielding the vinyl group directly, without the need to condense with formaldehyde.

The oxazolines produced by these and other methods all contain a vinyl group in a position alpha to the ring. Although this alpha vinyl group imparts to the oxazoline monomer some air-dry capabilities, these would be enhanced if the unsaturation, while still alpha to the ring, were not terminal.

SUMMARY OF THE INVENTION

There is provided by the present invention an oxazoline diester, capable of rapid air-drying, of the formula

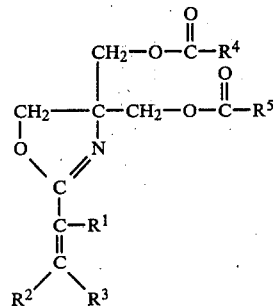

wherein $R^1$ and $R^2$ are the same or different and are H, aryl, or $C_1$-$C_4$ alkyl; $R^3$ is alkyl, aryl, or carboxyl; and $R^4$ and $R^5$ are the same or different and are each the residue of an aliphatic carboxylic acid that has 6 or more carbon atoms or an aromatic carboxylic acid.

A process for preparing the above monomeric oxazoline diesters is also provided. The process comprises the steps of (a) reacting 0.8-1.25 moles of tris(hydroxymethyl) aminomethane with 1 mole of a non-terminally unsaturated carboxylic acid of the formula

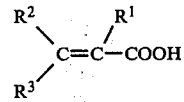

where $R^1$ and $R^2$ are the same or different and are H, aryl, or $C_1$-$C_4$ alkyl and $R^3$ is alkyl, aryl, or carboxyl; and (b) esterifying the reaction product of (a) with an acid selected from the group consisting of aliphatic carboxylic acids having at least 6 carbon atoms, aromatic carboxylic acids, and mixtures of these in a molar ratio of said acid to said reaction product of about 2:1 wherein reactions (a) and (b) are carried out at atmospheric pressure and reflux conditions and in the absence of a polymerization inhibitor, and wherein the oxazoline diester is produced in monomeric form.

DETAILED DESCRIPTION OF THE INVENTION

The oxazoline diesters of the present invention are structurally and chemically characterized, and distinguished from prior art vinyl oxazolines, by the presence of the non-terminal, alpha-ethylenic unsaturation. It has been found that monomeric oxazolines having such a non-terminal carbon-carbon double bond are unexpectedly superior to the heretofore used vinyl oxazolines as air-drying reactive diluents. The oxazolines of this invention are also capable of being polymerized at the alpha-ethylenic unsaturation to form higher molecular weight resins. These resins can also be air dried if either of the two ester groups of the oxazoline contains carbon-carbon unsaturation.

The monomeric oxazoline diester of this invention is prepared by reacting tris(hydroxymethyl) aminomethane with a non-terminally unsaturated acid in a molar ratio of about 0.8-1.25 moles of the amine per mole of acid. The acid is an alpha, beta, ethylenically-unsaturated carboxylic acid having the general formula

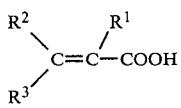

where $R^1$ and $R^2$ are the same or different and are H, aryl, or $C_1$-$C_4$ alkyl and where $R^3$ is alkyl, aryl, or carboxyl. It is preferred in all cases that the alkyl groups present, if any, be methyl, ethyl, or propyl and that the aryl group be phenyl. The cis and trans isomers of acids within the above structure are also contemplated for use in the present invention. Examples of preferred acids are crotonic acid, isocrotonic acid, angelic acid, tiglic acid, cinnamic acid, allocinnammic acid, citraconic acid, and mesaconic acid. Most preferred acids are those in which $R^1$ and $R^2$ are H or methyl and $R^3$ is lower alkyl. Such an acid is crotonic acid.

The reaction between the acid and the tris(hydroxymethyl) aminomethane is carried out in an inert organic solvent, examples of which are aromatics, esters, ethers, ketones, or alcohols. Specific examples are benzene, toluene, xylene, butyl acetate, ethylene glycol monoethyl ether acetate, acetone, methylethyl ketone, methylisobutyl ketone, ethanol, and butanol.

The reaction is conducted in a standard reaction vessel equipped with a reflux condenser and agitation means. The reactants are heated to reflux, at atmospheric pressure, and these conditions are maintained throughout the reaction. The generated water is removed continuously. As the reaction progresses, the reactants first condense to form an amide of the formula

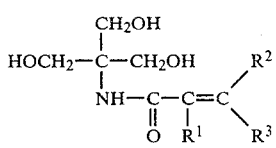

which further dehydrates, leading to ring closure, to form a monomeric oxazoline of the formula

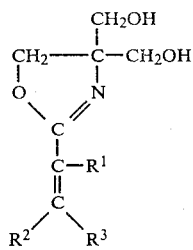

wherein $R^1$, $R^2$, and $R^3$ are as previously described. The amine intermediate is not separated, and the reaction proceeds directly through the intermediate stage to the formation of the oxazoline.

The reaction progresses without the presence of a catalyst, and as has further been found, the monomeric oxazolines of this invention, prepared as described above, have no tendency to polymerize during the prolonged heating step necessary to effect ring closure. Such premature polymerization has heretofore led to reduced yields of the desired, pure, monomeric oxazoline and has made recovery of the actual yield difficult. The use of polymerization inhibitors has previously been necessary, therefore, to produce monomeric oxazolines, but is not necessary in the practice of the present invention.

When the tris(hydroxymethyl) aminomethane and acid are fully reacted to form the oxazoline, as determined by monitoring the water collection, the oxazoline monomer is further esterified with additional carboxylic acids. In this esterification, the reactants are present in a molar ratio of acid to oxazoline of about 2:1. These esterifying carboxylic acids can be aliphatic or aromatic. The oxazoline has two hydroxyl groups available for esterification, and the esterifying acids may be the same or different.

The aliphatic acid can be any saturated or unsaturated acid having at least 6 carbon atoms. Fatty acids are preferred for use, and the unsaturated fatty acids are most preferred, to impart further air-drying capability to the oxazoline. Examples of useful acids are the fatty acids of soya oil, tall oil, linseed oil, tung oil, peanut oil, cottonseed oil, castor oil, coconut oil, olive oil, and palm oil. Examples of useful aromatic acids are benzoic acid, toluic acid, and phenylacetic acid.

The esterification reaction can be and preferably is conducted in the same vessel as was the formation of the oxazoline. The esterifying acids are charged into the vessel and mixed with the oxazoline. Heat is applied, and the mixture then brought to reflux at atmospheric pressure. These conditions are maintained until the reaction is completed. During the reaction, the water of esterification is removed continuously. It has been found that even in the absence of polymerization inhibitor, this esterification also can proceed without the occurrence of polymerization of the oxazoline through the alpha-unsaturation.

The final product, the oxazoline diester, is represented by the formula

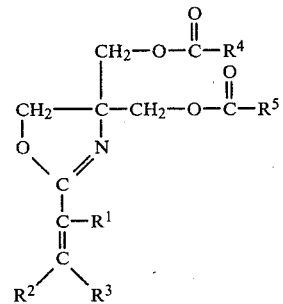

wherein $R^4$ and $R^5$ are the residue of the above-described esterifying acids and $R^1$-$R^3$ have the previously expressed meanings.

As mentioned earlier, the oxazoline diester is suitable for use as a coating material either in monomeric form as an air-dryable reactive diluent, or in polymeric form, after controlled homopolymerization or co-polymerization with compatible monomers, as a constituent of a film-forming resin. The polymerization can be accomplished in a manner similar to that disclosed in Purcell, U.S. Pat. No. 3,248,397, although conventional polymerization methods can also be used. The polymerization takes place through the unsaturation that is alpha to the ring, but the oxazoline will still impart air-drying capabilities to the resin when $R^4$ or $R^5$ contain carbon-carbon unsaturation.

The following example illustrates the best mode of the invention.

EXAMPLE

Xylene, 34 parts by weight, tris(hydroxymethyl) aminomethane, 476 parts by weight; and crotonic acid, 344 parts by weight, are charged to a reaction vessel equipped with an agitator and reflux condenser. The mixture is heated at atmospheric pressure, to reflux, at which point the vapor temperature is 117° C. and the batch liquid temperature is 136° C. Reflux conditions are maintained and the water formed is collected continuously until the reaction is completed, as determined by monitoring the water production. At completion, a total of 128.9 parts by weight of water are collected and the vapor temperature reaches 125° C.

At this point, the heat is discontinued and 2240 parts by weight of soybean oil acids are added. Heating is resumed to reach reflux, where the vapor temperature is 92° C. and the batch liquid temperature is 165° C. Reflux is maintained until the reaction is completed, determined by monitoring the water by-product. At completion, the final vapor temperature is 98° C. and the final batch temperature is 230° C. A total of 281 parts by weight of water is recovered.

The final product mixture has an acid number of 21, a Gardner-Holdt viscosity of A, and a solids content of 96% by weight.

What is claimed is:

1. An oxazoline diester, capable of rapid air-drying, of the formula

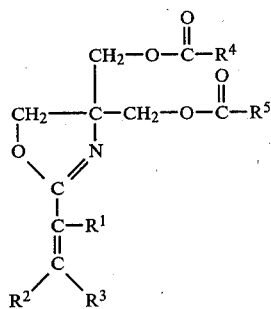

wherein $R^1$ and $R^2$ are the same or different and are H, aryl, or $C_1$–$C_4$ alkyl; $R^3$ is alkyl, aryl, or carboxyl; and $R^4$ and $R^5$ are the same or different and are each the residue of an aliphatic carboxylic acid that has 6 or more carbon atoms or an aromatic carboxylic acid.

2. The oxazoline diester of claim 1 in which $R^1$ and $R^2$ are hydrogen or methyl and $R^3$ is methyl, ethyl, or propyl.

3. The oxazoline diester of claim 2 in which $R^4$ and $R^5$ are the residue of fatty acids.

4. The oxazoline diester of claim 3 in which the fatty acids are from drying oils.

5. The oxazoline of claim 4 in which $R^1$ and $R^2$ are hydrogen.

6. A process for preparing a monomeric oxazoline diester comprising the steps of
   (a) reacting 0.8–1.25 moles of tris(hydroxymethyl) aminomethane with 1 mole of a non-terminally unsaturated carboxylic acid of the formula

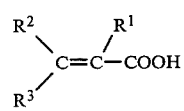

where $R^1$ and $R^2$ are the same or different and are H, aryl, or $C_1$–$C_4$ alkyl and $R^3$ is alkyl, aryl, or carboxyl; and
   (b) esterifying the reaction product of (a) with an acid selected from the group consisting of aliphatic carboxylic acids having at least 6 carbon atoms, aromatic carboxylic acids, and mixtures of these in a molar ratio of said acid to said reaction product of about 2:1 wherein reactions (a) and (b) are carried out at atmospheric pressure and reflux conditions and in the absence of a polymerization inhibitor, and wherein the oxazoline diester is produced in monomeric form.

7. The process of claim 6 in which $R^1$ and $R^2$ are hydrogen or methyl and $R^3$ is methyl, ethyl, or propyl.

8. The process of claim 7 in which the non-terminally unsaturated acid is selected from the group consisting of crotonic acid, isocrotonic acid, angelic acid, and tiglic acid.

9. The process of claim 8 in which the esterifying acid is introduced in the form of a drying oil.

* * * * *